United States Patent
Romagnani (12)

(10) Patent No.: US 6,197,524 B1
(45) Date of Patent: Mar. 6, 2001

(54) METHODS FOR DETECTING, IDENTIFYING, ISOLATING, AND SELECTIVELY LABELLING AND TARGETING TH1 LYMPHOCYTE BY MEANS OF THE LAG-3 PROTEIN

(75) Inventor: Sergio Romagnani, Florence (IT)

(73) Assignees: Institute National de la Sante et de la Recherche Medicale, Paris; Institut Gustave Roussy, Villejuif Cedex, both of (FR); Applied Research Systems, ARS Holding N.V., Curacao (AN)

( * ) Notice: Subject to any disclaimer, the term of this patent is extended or adjusted under 35 U.S.C. 154(b) by 0 days.

(21) Appl. No.: 08/983,576

(22) PCT Filed: Jul. 19, 1996

(86) PCT No.: PCT/US96/11994

§ 371 Date: Apr. 15, 1998

§ 102(e) Date: Apr. 15, 1998

(87) PCT Pub. No.: WO97/03695

PCT Pub. Date: Feb. 6, 1997

Related U.S. Application Data

(60) Provisional application No. 60/001,367, filed on Jul. 21, 1995, and provisional application No. 60/002,683, filed on Sep. 21, 1995.

(51) Int. Cl.$^7$ ........................ G01N 33/53; G01N 33/536; G01N 33/564; G01N 33/577

(52) U.S. Cl. ........................... 435/7.1; 435/7.2; 435/7.24; 436/501; 436/506; 436/536; 436/811

(58) Field of Search ............................ 435/7.2, 7.1, 7.24; 436/501, 506, 536, 811; 530/388.25, 388.22, 388.75, 389.3, 389.6

(56) References Cited

U.S. PATENT DOCUMENTS 5,874,250 * 2/1999 Hercend et al. .................... 435/69.3

FOREIGN PATENT DOCUMENTS 9110682  7/1991  (WO).
9530750  11/1995 (WO).

OTHER PUBLICATIONS

Huard et al., "Lymphocyte–activation gene 3/major histocompatibility complex class II interaction modulates the antigenic response of CD4 T lymphocytes", Eur. J. Immunol., 24:3216–3221, (1994).

Del Prete et al., "Preferential expression of CD30 by human CD4 T cells producing Th2–type cytokines" The FASEB Journal, 9:81–86, (1995).

Maggi et al., "Reciprocal Regulatory Effects of IFN–y and IL–4 on the in vitro Development of Human Th1 and Th2 Clones", The Journal of Immunology, vol. 148, No. 7, pp. 2142–2147, (1992).

Romagnani et al., "Human Th1 and Th2 cells", Allergologie, vol. 19, No. 4, pp. 175–179, (1996).

Annuziato, F. et al., "Expression and release of LAG–3–encoded protein by human CD4$^+$ T cells are associated with IFN–gamma production.", The FASEB Journal, vol. 10, pp. 769–776 (1996).

Waldmann, T., "Monoclonal antibodies in diagnosis and therapy.", Science, vol. 253, pp. 1657–1662 (1991).

Harris, W. et al., "Therapeutic antibodies—the coming of age.", Forum–Tibtech, vol. 11, pp. 42–44 (1993).

Foon, K. et al., "Biological response modifiers: the new immunotherapy.", Cancer Research, vol. 49, pp. 1621–1639 (1989).

Riddell, S. et al., "Restoration of viral immunity in immunodeficient humans by the adoptive transfer of T cell clones.", Science, vol. 257, pp. 238–241 (1992).

Bruijin, M. et al., "Peptide loading of empty major histocompatibility complex molecules on RMA–A cells allows the induction of primary cytotoxic T lymphocyte responses.", Eur. J. Immunol., vol. 21, pp. 2963–2970 (1991).

Macatonia, S. et al., "Primary stimulation by dendritic cells induces antiviral proliferative and cytotoxic T cell responses in vitro." J. Exp. Med., vol. 169, pp. 1255–1264 (1989).

Oldstone, M. et al., "Cytoimmunotherapy for persistent virus infection reveals a unique clearance pattern from the central nervous system.", Nature, vol. 321, pp. 239–243 (1986).

Kast, W. et al., "Eradication of adenovirus E1–induced tumors by E1A–specific cytotoxic T lymphocytes.", vol. 59, pp. 603–614 (1989).

Treibel, F. et al., "LAG–3, a novel lymphocyte activation gene closely related to CD4.", J. Exp. Med., pp. 1393–1405 (1989).

Baixeras, E. et al., "Characterization of the lymphocyte activation gene 3–encoded protein. A new ligand for human leukocyte antigen class II antigens.", J. Exp. Med., vol. 176, pp. 327–337 (1992).

(List continued on next page.)

Primary Examiner—Ronald B. Schwadron
(74) Attorney, Agent, or Firm—Browdy and Neimark

(57) ABSTRACT

The lymphocyte ativation gene (LAG-3) is a member of the immunoglobulin superfamily that is selectively transcribed in human activated T and NK cells. Surface LAG-3 expression correlated with IFN-γ but not IL-4, production in antigen-stimulated T-cells and it was up-regulated by IL-12 and is preferentially associated with CD4+ T-cells producing Th1-type cytokines. The presence of LAG-3 on the surface of Th1 lymphocytes is used as a marker to detect and identify Th1 lymphocytes and differentiate them from Th2 lymphocytes. Monoclonal antibodies to LAG-3 are used in methods of detecting and isolating Th1 cells as well as methods of diagnosing Th1-mediated disease. The present invention also relates to methods of treating infectious diseases, cancer, and disorders assocated with Th1/Th2 imbalance.

1 Claim, 6 Drawing Sheets

OTHER PUBLICATIONS

Kuchroo, V. et al., "B7–1 and B7–2 costimulatory molecules activate differentially the Th1/Th2 developmental pathways: application to autoimmune disease therapy.", Cell, vol. 80, pp. 707–718 (1995).

Liblau, R. et al., "Th1 and Th2 CD4+ T cells in the pathogenesis of organ–specific autoimmune diseases.", Immunology Today, vol. 16, No. 1, pp. 34–38 (1995).

Lanzavecchia, A. et al., "Identifying strategies for immune intervention.", Science, vol. 260, pp. 937–944 (1993).

* cited by examiner

○ Th1 CLONES
● Th2 CLONES

METHODS FOR DETECTING, IDENTIFYING, ISOLATING, AND SELECTIVELY LABELLING AND TARGETING TH1 LYMPHOCYTE BY MEANS OF THE LAG-3 PROTEIN

CROSS-REFERENCE TO RELATED APPLICATIONS

This is a 371 national stage application from PCT/US96/11994, filed Jul. 19, 1996, which claims benefit of priority from provisional applications 60/001,367, filed Jul. 21, 1995, and 60/002,683, filed Sep. 21, 1995.

BACKGROUND OF THE INVENTION

1. Field of the Invention

The present invention relates to methods for detecting, identifying, isolating, and selectively labelling and targeting TH1 lymphocytes and, more particularly, to such methods which use the presence of LAG-3 protein on the surface thereof as markers for the identity of TH1 lymphocytes. The present invention also related to methods of treating infectious diseases, cancer, Th1-mediated diseases and disorders associated with an imbalance of Th1 and Th2 cells.

2. Description of the Background Art

The lymphocyte activation gene (LAG-3) is a member of the immunoglobulin superfamily, that is selectively transcribed in human activated T (both $CD4^+$ and $CD8^+$) and NK cells (Triebel et al, 1990; see also WO91-110682). The sequence data, the compared exon/intron organization, and the chromosomal localization revealed that LAG-3 is closely related to CD4 (Baixeras et al, 1992). The close relationship between LAG-3 and CD4 was further strengthened by the demonstration that both share the same ligand, i.e., MHC class II molecules (Baixeras et al, 1992). However, in contrast to CD4, LAG-3 does not bind the human immunodeficiency virus gp120 (Baixeras et al, 1992). In vivo, LAG-3 expression was neither found in primary lymphoid organs, such as spleen, mucosa-associated lymphoid tissue or normal lymph nodes. However, it was readily detected in inflamed tonsils, or lymph nodes with follicular hyperplasia, supporting the view that even in vivo LAG-3 is expressed following activation (Huard et al, 1994A) The physiological role of encoded LAG-3 protein is still unclear. Antigen-specific stimulation of T-cell clones in the presence of anti-LAG-3 monoclonal antibody (mAb) led to increased thymidine incorporation, higher expression of activation marker CD25 and enhanced cytokine production (Huard et al, 1994B). Accordingly, addition of a soluble recombinant form of LAG-3 inhibited antigen-specific T-cell proliferation, suggesting a regulatory role of LAG-3 in $CD4^+$ T-lymphocyte activation (Huard, 1995).

Studies of both murine and human $CD4^+$ T-cell clones have shown that $CD4^+$ T helper (Th) cells comprise functionally heterogenous populations based on their profile or cytokine production (Mosmann et al, 1986; Del Prete et al, 1991). Th1 cells produce interleukin (IL)-2, interferon (IFN)-γ and tumor necrosis factor (TNF)-β, whereas Th2 cells produce IL-4 and IL-5. In the absence of a prominent differentiation of Th1 or Th2 cells, the large majority of $CD4^+$ T-cells produce both Th1- and Th2-type cytokines (i.e., Th0 cells) (Mosmann et al, 1986; Del Prete et al, 1991; Sher et al, 1992; Romagnani, S., 1994). Recently, we have shown that human Th1 and Th2 clones not only exhibit different functional properties but also show differential expression of CD30 (Del Prete et al, 1995A), an activation marker belonging to the TNF receptor family (Smith et al, 1990).

It has been suggested that Th1 cells contribute to the pathogenesis of organ-specific autoimmune diseases while Th2 cells prevents them (Liblau et al, 1995). Thus, it would be useful to have a simple way to identify and isolate Th1 cells to the exclusion of Th2 cells.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It has now been discovered that the LAG-3 expression is preferentially associated with $CD4^+$ T-cells addressed to the production of Th1-type cytokines. Thus, LAG-3 expression can be used as a marker to detect and identify Th1 lymphocytes and differentiate them from Th2 lymphocytes. Monoclonal antibodies against LAG-3 can be used to detect and identify Th1 lymphocytes which express the LAG-3 protein.

Furthermore, the LAG-3 marker can be used to isolate Th1 cells from Th2 cells. It is known, for example, that Th1 cells contribute to the pathogenesis of organ-specific autoimmune diseases while Th2 cells prevent them. Thus, autologous T-cells from autoimmune disease patients can be subjected to separation into Th1 and Th2 rich fractions ex vivo and the Th2 cells reinfused to help fight the autoimmune disease. The same is true for any disease or condition which is preferentially mediated by Th1 cells, such as contact dermatitis.

Another therapeutic method using the discovery that LAG-3 is a selective marker for Th1 lymphocytes is by means of immunotoxins using monoclonal antibodies specific for the extracellular portion of the LAG-3 protein. If a toxic moiety is attached to such antibodies by means well known in the art, Th1 lymphocytes can be selectively targeted for destruction. By thus effectively shifting the balance of $CD4^+$ helper T-cells from the Th1 type to the Th2 type, Th1 mediated diseases can be mitigated.

Alternately, the anti-LAG-3 monoclonal antibodies is used to modulate the balance of Th1/Th2 cell population and polarize the differentiation of Th0 cells to Th1 cells.

Labelled monoclonal antibodies against LAG-3 can be used to selectively label Th1 cells. Thus, if a radioactive label is used, the location of Th1 cells can be followed by appropriate viewing means.

Another aspect of the present invention is that anti-LAG-3 antibodies, either immobilized on a solid support or labeled with a fluorescent compound, can bind Th1 cells to separate Th1 cells from Th2 cells.

A further aspect of the present invention is to expand the isolated or enriched Th1 or Th2 cells for reinfusion back into a patient from whom they were obtained in order to increase phagocyte dependent or phagocyte independent host defenses, respectively.

In addition, the present invention also provides a method for diagnosing Th1-mediated diseases or disorders by measuring in a fluid sample from a patient the amount of soluble LAG-3 that is bound to soluble LAG-3 specific antibody.

Accordingly, the present invention is directed to all of the above methods for using the discovery that the LAG-3 protein is preferentially associated with Th1 lymphocytes.

DETAILED DESCRIPTION OF THE INVENTION

Figure 1A:
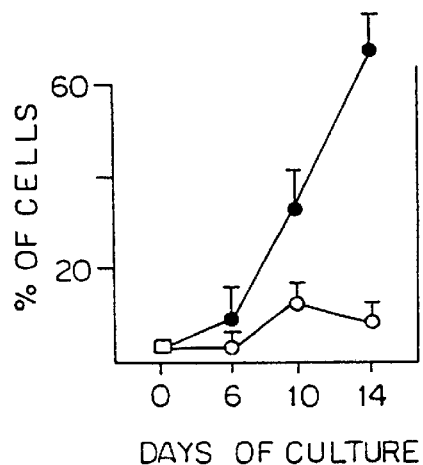
FIGS. 1a–1d show the kinetics of membrane LAG-3 or CD30 expression and cytokine production by antigen-activated human T-cells. T-cell lines specific for SK (upper part) or Der p 1 (lower part) were generated from PBMC of normal subjects, as described in Example 1. On day 0 and after 6, 10 and 14 days of culture, viable T-cell blasts were washed, counted, resuspended in fresh medium, and assessed for both membrane LAG-3 (•) and CD30 (○) expression by flow cytometry, as described in Example 1 and shown in the left-side graphs. At the same time intervals, T-cells ($10^6$/ml) from each line were also restimulated for 24 hr with PMA plus anti-CD3 antibody and culture supernatants assessed for IFN-γ (•) and IL-4 (○) content by appropriate ELISAs, as described in Example 1 and shown in the right-side graphs. The results represent mean values ± SE obtained with cells from three different donors.
Figure 1B:
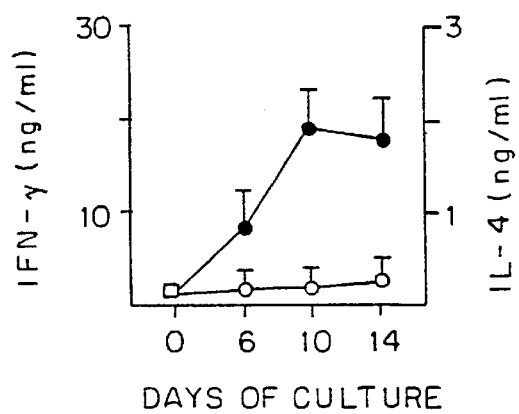
Figure 1C:
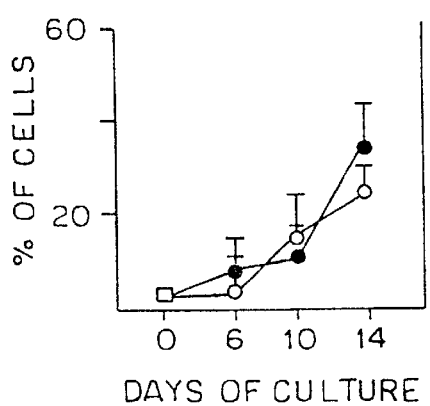
Figure 1D:
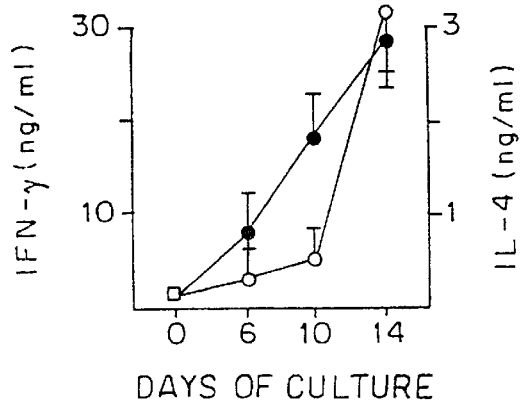

LAG-3 expression, like CD30, is preferentially related to the Th1 phenotype of cytokine secretion. Test results have demonstrated that LAG-3 correlates with IFN-γ, but not IL-4, production in antigen-stimulated T-cells and it is upregulated by IL-12 addition in bulk culture. Moreover, most Th1 and Th0 clones express membrane LAG-3 and release detectable amounts of soluble LAG-3, whereas only a few Th2 clones show LAG-3 expression and release. Thus, LAG-3 expression is preferentially associated with $CD4^{30}$ T-cells addressed to the production of Th1-type cytokines.

The results described in the present examples demonstrate that LAG-3, a member of the Ig superfamily selectively transcribed on activated human T and NK cells (Triebel et al, 1990), is preferentially expressed by $CD4^{30}$ T-cells producing Th1-type cytokines. First, LAG-3 expression in short-term cultures correlated with the ability of antigen-activated T-cells to produce IFN-γ, but not with IL-4 production. Second, the appearance of LAG-3 on antigen-stimulated T-cells was up-regulated by IL-12, a powerful Th1-inducing cytokine (Manetti et al, 1993; Manetti et al, 1994), whereas it was not influenced by IL-4 that in contrast promotes the development of Th2 cells (Maggi, 1992). Most importantly, LAG-3 was expressed by the great majority of $CD4^{30}$ T-cell clones with established Th1 or Th0 profile of cytokine secretion, but it was virtually absent on Th2 clones. Finally, LAG-3-related soluble molecule(s) were released by activated $CD4^{30}$ T-cells able to produce IFN-1 or both IFN-γ and IL-4, but not by $CD4^{30}$ T-cells inducible to the production of IL-4 alone.

LAG-3 shows a close relationship with CD4 suggesting that both molecules originate from a common evolutionary ancestor (Triebel et al, 1990). Moreover LAG-3 and CD4 proteins share a common ligand (i.e., MHC class II antigens) (Baixeras, 1992). Thus, LAG-3 may be effective in contributing to the regulation of activated T-cell interactions with antigen-presenting cells, which are known to express high numbers of MHC class II molecules on their surface. On the other hand, this molecule may also regulate T-cell/T-cell interactions, inasmuch as activated T-cells also express class II molecules. The strong association of LAG-3 expression with the ability of activated T-cells to produce IFN-γ and its loss by activated T-cells addressed to the selective production of IL-4 suggests a common or crossed regulation of both LAG-3 and IFN-γ gene transcription.

The demonstration that LAG-3 is preferentially expressed, and its soluble form released, by $CD4^+$ T-cells able to produce Th1-type cytokines may also allow further insights into the mechanisms involved in the development of Th1 or Th2 pathway. Th1 and Th2 cells indeed represent two extremely polarized forms of the effector immune response against exogenous offending agents (Mosmann et al, 1986; Del Prete, 1991; Sher et al, 1992; Romagnani, S., 1994). Th1 cells are responsible for macrophage activation (via IFN-γ) and delayed type hypersensitivity reactions and in the murine system stimulate the production of antibodies of the IgG2a class, which are effective at activating complement and opsonizing antigens for phagocytosis (Sher et al, 1992; Romagnani, S., 1994). Thus Th1 cells mainly trigger phagocyte-mediated host defense against infections with intracellular microbes which, in turn, tend to induce Th1-type responses (Sher et al, 1992; Romagnani, S., 1994). On the other hand, Th2 cells induce the production of IgE and IgG1 antibodies (via IL-4 and IL-13), favor the growth of mast-cells (via IL-3, IL-4 and IL-10), the differentiation and activation of eosinophils (via IL-5), and are capable of inhibiting several macrophage functions (via IL-4, IL-13 and IL-10). Therefore, Th2 cells are prevalently involved in phagocyte-independent host defense, e.g., against helminths, as well as in the response of atopic people to common environmental allergens, which is mediated by IgE antibodies and eosinophils (Sher et al, 1992; Romagnani, S., 1994). The nature of Th1 or Th2 polarizing signals is not yet fully understood. In both mice and humans, IL-12 produced by macrophage and B cells promotes Th1 differentiation (Manetti et al, 1993; Manetti et al, 1994; Hsieh et al, 1993), whereas early IL-4 production at the time of antigen presentation appears to be the most dominant factor in determining the likelihood for Th2 polarization of naive Th cells (Maggi et al, 1992; Swain, S. L., 1993; Seder et al, 1992). However, a role for antigen-presenting cells A their co-stimulants has also been suggested (Reiner et al, 1993). In this regard, it is noteworthy that interaction between CD30, a preferential marker of Th0/Th2 cells (Del Prete et al, 1995A) and the CD30 ligand, which is expressed not only on T-cells, but also on macrophages and B lymphocytes (Smith et al, 1990; Maggi et al, 1995), favors the preferential development in vitro of T-cells producing Th2-type cytokines (Del Prete, 1995B). Inasmuch as LAG-3 expression reflects a selective differentiation and/or activation pathway of T-cells producing Th1-type cytokines, it will be of interest to determine the function of the LAG-3 and its ligand in the control of expression of multiple cell surface molecules and cytokines by T-cells.

The detection of surface LAG-3 expression and/or measurement of its soluble form is to be utilized as a marker for the recognition of Th1/Th0-mediated immune reactions in tissues and/or biologic fluids in different diseases. Non-limiting examples of such Th1-mediated diseases or disorders are reviewed in Mosmann and Sad (1996). It is noted that CD30+, a preferential marker of activated Th2-like cells in vitro (Del Prete, 1995A), is never expressed in normal subjects in vivo, but high numbers of CD4+ CD30+ T-cells can be found in the lymph nodes of children with Omenn's syndrome (Romagnani et al, 1995; Chilosi et al, submitted) and in the lesional skin of patients with atopic dermatitis. More importantly, high levels of soluble CD30 are present in the serum of patients with Omenn's syndrome (Romagnani, 1995) or with severe atopy (Romagnani, 1995), as well as in those of subjects with other pathological conditions, such as HIV infection (Pizzolo, 1994), systemic lupus erythematosus (Cappio et al, 1995), and measles virus infection (Vinante et al), in which predominant activation of Th0/Th2 cells has been suggested (Clerici et al, 1993; Mills, J. A., 1994; Griffin et al, 1993). As with CD30, LAG-3 was never found in normal lymphoid organs, but it was readily detected in inflamed tonsils, or lymph nodes with follicular hyperplasia (Huard et al, 1994) , suggesting that even in vivo, it is only expressed following activation.

Interestingly, in recent experiments, the laboratory of the present inventors has found elevated levels of soluble LAG-3, but not of soluble CD30, in the sera of most patients with multiple sclerosis, which is considered as a prototype of Th1-mediated disorders (Selmaj et al, 1991). The higher levels of soluble LAG-3 in the blood of multiple sclerosis patients versus healthy individuals suggest a possible link between the disease status and the soluble LAG-3 production in the body. Conversely, a high percentage of Th1 LAG-3 positive CD4 lymphocytes were found in the cerebrospinal fluid of multiple sclerosis patients (Annunziato et al., 1996). High numbers of Th1-like T-cell clones could indeed be generated from the cerebrospinal fluid of two patients with this disease that consistently expressed surface LAG-3 and released high concentrations of soluble LAG-3 in their supernatants. Based on these findings, the combined measurement of soluble CD30 and soluble LAG-3 represents a simple practical way to assess the imbalance of the effector immune response towards the Th2 or the Th1 profile.

Monoclonal antibodies against the surface portion of LAG-3 may be obtained by the processes described in WO91-10682 and in U.S. Pat. application Ser. No. 08/394, 442 filed Feb. 24, 1995, the entire contents of which are hereby incorporated herein by reference. Such monoclonal antibodies, or fractions thereof such as the Fab or F(ab')$_2$ fractions, or the variable portions of the heavy or light chains thereof, or single chain antibodies, or any other molecule which includes the binding portion of such antibodies, can be used to identify, detect, label and/or target Th1 cells because of their preferential expression of LAG-3. The present invention is intended to comprehend all known means of immunodetection and labelling, e.g., enzyme, fluorescent, chemiluminescent, bioluminescent or radioactive, as are well known in the art. Such techniques are known, for example, from Harlow et al "Antibodies: A Laboratory Manual", Cold Spring Harbor Laboratory, 1988, "Current Protocols in Immunology", eds. Coligan et al., Wiley & Sons, Inc. 1992–1996, and many other sources well known to those of ordinary skill in the art. Thus, it is well within the skill of those in the art to detect Th1 cells and utilize measurement of the amount of Th1 cells or soluble LAG-3 in a biological sample as a marker for diagnosing a Th1-mediated disease or disorder.

The detection of elevated levels of soluble LAG-3 in the blood of a patient relative to healthy individuals is indicative of the presence of a Th1-mediated disease or disorder, and in particular, multiple sclerosis. This correlation of elevated soluble LAG-3 levels with Th1-mediated diseases and disorder can be used as a diagnostic test in a sample of human fluid. The sample is reacted with an antibody, or fragment thereof, specific for soluble LAG-3, and the amount of soluble LAG-3 bound to the specific antibody is measured by techniques well-known in the art.

Besides using monoclonal antibodies, if a ligand for LAG-3 is found which is sufficiently selective, such ligand can in also be used for the detection, identification, labelling and/or targeting of Th1 lymphocytes in accordance with the present invention.

Antibodies specific to LAG-3 can be immobilized on a solid support, preferably a chromatography column, magnetic or paramagnetic beads, or a petri dish (Current Protocols in Immunology, Vol.2, units 7.3 and 7.4, Wiley & Sons, Inc. 1992–1996), and used as an affinity support to separate Th1 and Th2 cells based on binding to the anti-LAG-3 antibodies immobilized on the solid support. For instance, a sample containing a mixture of Th1 and Th2 cells can be contacted with such a solid support having anti-LAG-3 antibodies immobilized thereon to bind Th1 cells. Th2 and other cells in the sample which do not have LAG-3 on their surface remain unbound and can be readily removed by elution, washing, etc. Alternatively, Th1 cells bound to anti-LAG-3 antibodies immobilized on magnetic or paramagnetic beads can be removed instead to provide isolated or enriched Th1 cells. The Th1 cells bound to the immobilized anti-LAG-3 antibodies can then be unbound and isolated. Likewise, Th2 cells that are not bound to the immobilized anti-LAG-3 antibodies are thus separated from Th1 cells and can be used as a LAG--Th2 cell-enriched population.

Th1 cells can also be separated from Th2 cells by means of a fluorescence activated cell sorter (FACS) device commercialized by various instrument suppliers including Becton Dickinson. Anti-LAG-3 antibodies, or fragments thereof, labeled with a fluorescent compound is reacted with a sample containing Th1 and Th2 cells to bind Th1 cells (Current Protocols in Immunology, unit 5, supra). Passage of the sample reacted with labeled antibodies Th1 cells bound to the fluorescently labeled antibodies from other cells, e.g. Th2 cells. This is another non-limiting example of separating Th1 and Th2 cells to provide a Th1 (or Th2) enriched population for ex vivo expansion in methods of treating diseases and disorders where reinfusion back into a patient from whom the sample was obtained increases the patient's phagocyte dependent host defense (in the case of Th1 reinfusion) or phagocyte independent host defense (in the case of Th2 reinfusion).

Furthermore, the present invention also relates to methods of treating infectious diseases, cancer, Th1-mediated diseases and disorders associated with an imbalance in the population of Th1 and Th2 cells. Mosmann and Sad (1996) reviews some of these diseases and disorders. For example, autoimmune diseases, such as multiple sclerosis (MS), type 1 diabetes mellitus (IDDM), rheumatoid arthritis (RA), and transplant rejection involve an imbalance in Th1/Th2 cell population (too much Th1) Thus, depending on the imbalance, ie., low relative amounts of Th1 or Th2 cells in the disease or disorder, administration of an expanded pool of Th1 or Th2 cells derived from the patient to be treated can be administered so as to reduce the imbalance of Th1 or Th2 cells.

For diseases and disorders where it is desired to raise the level of Th1 cells, a fluid sample from the patient to be treated that contains Th1 and Th2 cells is obtained, and the Th1 cells are isolated as discussed above by binding to immobilized anti-LAG-3 antibodies and then recovered off the solid support or by binding to fluorescently labeled anti-LAG-3 antibodies and sorted by passage through a FACS device. These isolated Th1 cells, separated from Th2 cells, can then be expanded ex vivo by standard techniques well known in the art, i.e., ex vivo bone marrow progenitor expansion techniques and ex vivo expansion of T cells for adoptive therapy (Macatonia et al., 1989; De Bruijn et al., 1991; Oldstone et al., 1986; Kast et al., 1989; Riddell et al., 1992), and then reinfused back into the same patient to elevate the level of Th1 cells. Thus, reinfusion of expanded Th1 cells increases the phagocyte host defense (cell mediated immunity) of the patient.

Likewise, for diseases and disorders where it is desired to raise the level of Th2 cells, i.e., allergy, a fluid sample obtained from a patient and containing Th1 and Th2 cells is also contacted with immobilized anti-LAG-3 antibodies. However, in this case, it is the unbound Th2 separated from Th1 cells that are to be used in ex vivo expansion. Reinfusion of the expanded Th2 cells back into the patient from whom the Th2 cells were derived, increases the phagocyte independent host defense (humoral immunity) of the patient.

The mAbs which are used in the processes of the present invention can be conjugated to cytotoxic agents and used as immunotoxins (see, for example, Vitetta et al., Science 238:1098–1104 (1987)), or incorporated onto the surface of liposomes containing anti-T-cell drugs or toxins to specifically target such drugs or toxins to Th1 cells. As used herein, the term "immunotoxin" refers to a conjugate or construct of an antibody with one or more toxins, drugs, radionuclides, or cytotoxic agents. A toxic moiety can either be chemically conjugated to the antibody, or alternatively, can be ligated through recombinant DNA technology. In such a ligation, the DNA encoding the toxic protein or an active fragment thereof is ligated to the DNA encoding the entire, or a portion of, the mAb heavy chain, light chain, or both. Such genetic constructs and methods for making them are known in the art. Among the toxins that may be conjugated to the antibodies of the present invention are ricin, diphtheria toxin, Pseudomonas toxin, tumor necrosis factor-alpha, and others known in the art.

In a typical treatment using the anti-LAG-3 mAbs as immunotoxins, the antibody is conjugated to a toxin such as ricin that, alone, is toxic to all cells. By coupling the cytotoxic agent to the antibody, a high level of toxic efficacy can be achieved in a highly localized manner, against the target Th1 cell to which the antibody has delivered the toxin, with a sparing of neighboring cells to which the antibody did not bind. Th1 mediated diseases can be mitigated by effectively shifting the balance of CD4+ helper T-cells from the Th1 type to the Th2 type.

Alternatively, the anti-LAG-3 mAb can be used to modulate the balance of Th1/Th2 cell population. This strategy is exemplified by the experiences acquired with the B7/CTLA4 -CD28 ligand receptor system. Briefly, induction and activation of T lymphocyte require two signals from antigen presenting cells (APC), one being transduced via the T cell receptor/major histocompatibility complex interaction and the second via costimulatory molecules interaction. The latter signal involves at least 2 molecules expressed by APC, designated B7-1 and B7-2 which interact with their counterreceptors expressed by T cells, i.e. CD28 and CTLA4. Using antibodies against B7-1it has been reported that naive Th precursors are driven to the Th2 pathway while anti-B7-2 antibodies favors Th1 development (Kuchroo et al., 1995). In addition, administration of anti B7-1 antibodies has been shown to ameliorate an organ specific auto-immune disease, e.g. murine experimental autoimmune encephalomyelitis (EAE, the animal model for human multiple sclerosis) , whereas injection of anti-B7-2 antibodies significantly worsened the clinical signs of EAE. Moreover, it has been shown that reinfusion of T lymphocytes with a Th2 profile can prevent the induction of EAE.

In a similar manner, administration of an anti-LAG-3 antibody, or fragment thereof, can be used to increase Th1-mediated immune response (phagocyte dependent host defense). by polarizing the differentiation of Th0 precursor cells towards Th1 cells.

While the antibodies used for purposes of the present invention may be intact antibodies, preferably human monoclonal antibodies, it should be understood that it is the epitope binding site of the antibody which provides the desired function. Thus, besides the intact antibody, proteolytic fragments thereof such as the Fab or F(ab')$_2$ fragments can be used. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, Z. et al., Br. J. Cancer Suppl., 10:27–9 (1990); Gross, G. et al., Proc. Natl. Acad. Sci. USA, 86:10024–8 (1989)). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$–$V_L$ or single chain $F_v$). Both $V_H$ and $V_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

When used in the present specification and claims, the recitation "a molecule including the antigen-binding portion of an antibody" is intended to include not only intact immunoglobulin molecules of any isotype and generated by any animal cell line or microorganism, but also the reactive fraction thereof including, but not limited to, the Fab fragment, the Fab' fragment, the F(ab')$_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction.

In a pharmaceutical composition containing anti-LAG-3 antibodies, or fragments thereof, as an active ingredient for modulating the balance of Th1/Th2 cells in vivo, the dosage of the active ingredient and the pharmaceutically acceptable excipient or carrier in the pharmaceutical composition can be readily determined by those of skill in the art.

EXAMPLE 1

Materials and Methods

Reagents

Tetanus toxoid (TT) was obtained from Istituto Steroterapico Sclavo (Siena, Italy) Streptokinase (SK) was obtained from Behringwerke (Malburg, Germany). *Dermatophagoides pteronyssinus* group 1 (Der p1) was obtained from Lofarma Allergeni (Milano, Italy). PHA was purchased from GIBCO Laboratories (Grand Island, N.Y.). Anti-CD3 monoclonal antibody (mAb) was purchased from Ortho Pharmaceuticals (Raritan, N.J.). Anti-CD4 (Leu 3*a*, IgG1s), anti-CD8 (Leu 2*a*, IgG1), anti-CD56 (Leu 19, IgG1) and anti-CD14 (Leu M1, IgG2b) mAbs were purchased from Becton-Dickinson (Mountain View, Calif.) Anti-CD20 (B1, IgG2a) was purchased from Kontron Instruments (Zurich, Switzerland). Anti-CD30 (Ber-H2) mAb was purchased from Dako. The anti-LAG-3 mAbs recognizing three different epitopes of LAG-3 molecule (17B4, IgG1; and 11E3, IgG1) (Baixeras et al, 1992) were obtained from Ares Serono (Geneve, Switzerland). Hybridoma cell line 17B4 was deposited on Jul. 10, 1992, with Collection Nationale de Cultures de Microorganismes (CNCM) under the designation I-1240, and hybridoma cell line 11E3 was also deposited with CNCM on Jul. 20, 1995, under the designation I-1612. Recombinant IL-2 was a generous gift of Eurocetus (Milano, Italy). Recombinant IL-12 was a kind gift of G. Trinchieri (Wistar Institute; Philadelphia, Pa.).

Generation of Antigen-Specific T-Cell Lines and Clones.

Antigen-specific T-cell lines were generated according to a technique previously described (Del Prete et al, 1991; Del Prete, 1995A). Briefly, $10^6$ peripheral blood mononuclear cells (PBMC) in 2 ml RPMI 1640 medium supplemented with 2 mM L- glutamine, $2\times10^{-5}$ M 2-mercaptoethanol, and 5% human serum (complete medium) were stimulated in 24-well-flat-bottomed plates for 5 days with the antigen (SK, 100 IU/ml; Der p 1, 10 μg/ml; TT, 0.5 μg/ml). Human IL-2 (20 U/ml) was then added and cultures continued for additional 9 days. Viable T blasts were resuspended in complete medium and tested for their antigen specificity before cloning procedure. To assess the antigen specificity of T-cell lines, $2\times10^4$ T blasts were seeded in microplates and co-cultured for 48 h with irradiated (6,000 rad) autologous PBMC ($5\times10^4$) in the presence of medium alone or the appropriate antigen (SK, 100 IU/ml; Der p 1, 10 μg/ml; TT, 0.5 μg/ml) After a 16-h pulse with 0.5 μCi $^3$H-TdR (Amersham International), cultures were harvested and radioactivity measured by liquid scintillation. To generate T-cell clones, T blasts obtained from antigen-specific lines were seeded under limiting dilution conditions (0.3 cell/well) in 6 round-bottomed microwell plates containing $10^5$ irradiated (6,000 rad) allogeneic PBMC cells (as feeder cells) and PHA (1% vol/vol) in a final vol of 0.2 ml complete medium supplemented with IL-2 (20 U/ml) and 10% FCS (Hyclone Laboratories Inc., Logan, Utah), as reported elsewhere (Del Prete, 1991; Del Prete, 1995A) Growing microcultures were then supplemented, at weekly intervals, with IL-2 (20 U/ml) and $10^5$ irradiated feeder cells. The phenotype distribution of lines and clones was assessed by flow cytometer analysis. The antigen-specificity of clones was assessed by measuring $^3$H-TdR uptake after 60 h stimulation with the appropriate antigen under MHC-restricted conditions (Del Prete, 1991; Del Prete, 1995A). When stimulation index (ratio between the mean counts per minute obtained in cultures stimulated with APC plus antigen and the mean counts per minute obtained in cultures with APC alone) was greater than 10, responses were considered as positive.

Induction and Quantitation of Cytokine Production by T-Cell Lines and Clones

To induce cytokine production, $10^6$ T blasts from each line or clone were cultured in the presence of PMA (10 ng/ml) plus anti-CD3 mAb (100 ng/ml). After 24 h, culture supernatants were collected, filtered, and stored in aliquots at −70° until used. The quantitative determinations of IFN-γ and IL-4 were performed by commercial ELISAs (Cytoscreen, Biosource International, Camarillo for IFN-γ, Quantikine R & D Systems, Minneapolis for IL-4). Values of the cytokine content 3 SD over those of control supernatants obtained by stimulation of irradiated feeder cells alone, were regarded as positive.

Detection of Surface LAG-3 and CD30

Cell surface marker analysis of T-cell lines and clones was performed on a Cytoron Absolute cytofluorimeter (Ortho Pharmaceutical, Raritan, N.J.) by using FITC-conjugated anti-CD3, anti-CD4, anti-CD8, and anti-CD30 (Ber-H2; Dakopatts, Glostrup, Denmark). LAG-3 was detected by an indirect assay using unlabelled anti-LAG-3 mAb followed by FITC-conjugated anti-mouse IgG1 goat antiserum (Southern Biotechnology Associates Inc.; Birmingham, Ala.). Contemporaneous detection of CD30 and LAG was performed by using a FITC-conjugated anti-CD30 mAb (Ber-H2; Dako) and anti-LAG-3 (11E3) mAb followed by PE-conjugated anti-mouse IgG1 goat antiserum (Southern Biotechnology Associates Inc.).

mRNA Expression for LAG-3

LAG-3 mRNA expression was evaluated in T-cell clones by PCR technology, mRNA was extracted from T-cell blasts stimulated for 12 hr with PHA (1% v/v) and IL-2 (20 U/ml) by the Oligotex™ Direct mRNA kit (Qiagen Inc.; Chatsworth, Calif.) The first-strand cDNA was synthesized using 100 ng mRNA, reverse transcriptase, and oligo dT primer at 37° C. for 1 hr (RT-PCR kit, Stratogen; La Jolla, Calif.). The PCR amplification was conducted with 2.5 U of Taq polymerase, and 100 ng of each primer and consisted of 30 cycles of amplification, each cycle including denaturation at 94° C. for 1 min, annealing at 66° C. for 1 min, and extension at 72° C. for 2 min. The forward primer was TCTCTCAGAGCCTCCGACTGGGTCATTTTG (SEQ ID NO:1) and the reverse primer was TCCTGCAGATG-GATATGGCAGGTGTAGGTC (SEQ ID NO:2). The amplified products were run on a 1.5% agarose gel.

Assessment of Soluble LAG-3 Production by ELISA

Detection of soluble LAG-3 in the supernatants of T-cell clones was performed by an appropriate ELISA based on the use of a recombinant soluble LAG-3 derived molecule (sLAG-3D1-D2). sLAG-3D1-D2 was obtained from PCR amplified DNA fragment encoding for the two first immunoglobulin-like domains of LAG-3 and subcloned into the pCLH3AXSV2DHFR expression vector (Cole et al., 1993). The construct was used to transfect a DHFR deficient CHO cell line (DUKX-B11) (Urlaub and Chasin, 1980). The sLAG-3D1-D2-producing CHO cells were cultured in Wheaton bioreactor and sLAG-3D1-D2 molecule purified by capture step on fast SP-Sepharose column followed by immunopurification on a 17B4 mAb-Poros EP column. The resulting protein was found to be >90% pure by RP-HPLC and SDS-PAGE. For the assay, plate wells were coated with anti-LAG-3 (11E3; 10$\mu$g/ml on 0.2 M carbonate buffer, pH 9.6) mAb and then incubated for 12 hr with test samples or different dilutions (from 0.12 to 25 ng/ml) of sLAG-3D1-D2. After washings, biotinylated anti-LAG-3 (17B4) mAb (0.5 $\mu$g/ml) was added for additional 2 hr, the plates stained with substrate solution, and the reaction read at 492 nm.

Delayed Type Hypersensitivity Reaction

Six bred female Cynomolgus monkeys, about 2–3 years old, weighing around 2.6–2.9 kg, were housed individually in stainless cages. At Day 0, these monkeys were vaccinated once with $\geq$40 IU/monkey of tetanus vaccine (Tetatox Berna, lot no 13588) by intramuscular route. A first DTH reaction was induced 28 days later by applying the commercially available disposable applicator Multitest IMC (Pasteur-Merieux, lot L0157) including TT antigen on the left part of the abdomen. Monkeys were anaesthetised by an i.m. injection of 20 mg/kg of Kematine hydrochloride (Inoketam "500", Vibrac), their abdomen was clipped, cleaned and dried. Following the manufacturer's instructions, the applicator was pressed firmly to the skin for at least 5 seconds.

A second DTH reaction was induced at Day 56 using the same procedure used for the first DTH except that monkeys received, 30 min before application of the Multitest IMC on the right part of the abdomen, 10 mg/kg body weight of either anti-LAG-3 11E3 mAb (IgG1 ) or anti-FSH mAb (IgG1 ) as negative control by i.v. route.

Daily inspections for general clinical signs were performed up to the end of the study. The skin induration after DTH induction was measured after both the first and the second induction using a calliper. The greatest length of skin test reaction was measured followed by the greatest width bisecting the first measurement. Both measurements, were repeated twice starting 24 hours after induction until a negative response was obtained.

Results

Differential Expression of LAG-3 by SK- and Der pI-Activated T Cells

The kinetics of LAG-3 expression by T-cells activated in vitro with two different antigens (SK and Der p 1) was investigated and compared with the T-cell profile of cytokine production. These antigens were chosen because of their ability to expand T-cells with prevalent Th1-like or Th2-like profile, respectively (Manetti et al, 1993; Manetti et al, 1994; Maggi et al, 1992). To this end, PBMC from each of three donors were stimulated with SK or Der p 1 and the derived antigen-specific T-cell lines were tested for both LAG-3 expression and ability to produce IL-4 and IFN-$\gamma$ at 5, 10 and 15 days following antigenic stimulation. Both SK-specific and Der p 1-specific T-cell lines were also tested at the same time intervals for expression of surface CD30, an activation antigen preferentially associated with the production of Th2-type cytokines (Smith et al, 1990). As shown in FIGS. 1a–1d, SK-specific T-cells produced high amounts of IFN-$\gamma$, but no or low amounts of IL-4, and showed strong LAG-3, but poor CD30, expression. In contrast, Der p 1-specific T-cells, that produced high amounts of IL-4 in addition to IFN-$\gamma$, showed higher CD30 and lower LAG-3 expression than SK-specific T-cells. Double staining experiments revealed that most T-cell blasts from SK-specific T-cell lines were CD30$^-$LAG-3$^+$, whereas the majority of T-cell blasts from Der p 1-specific T-cell lines were CD30$^+$LAG-3$^{31}$ or CD30$^+$LAG-3$^+$.

Up-Regulation of LAG-3 Expression by IL-12

Figure 2C:
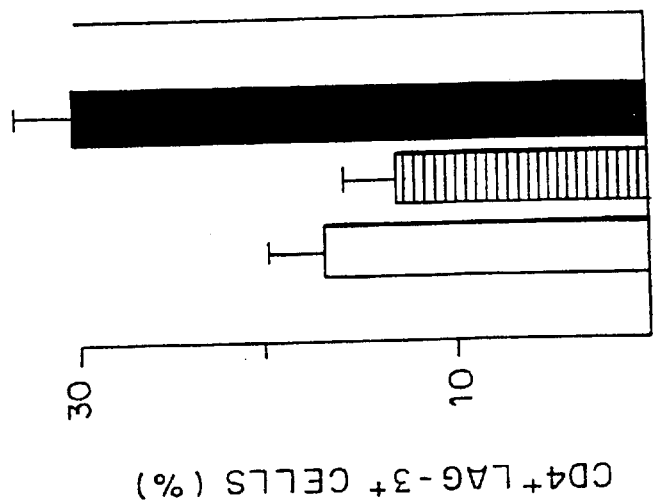
FIGS. 2a–2c show the up-regulation of membrane LAG-3 expression by IL-12. T-cell lines specific for tetanus toxoid (TT) generated from PBMC of normal subjects in the absence (□) of IL-4 and IL-12 or in the presence of IL-4 (▤) or in the presence of IL-12 (▦), as described in Example 1. On day 10 of culture, viable T-cell blasts were assessed for production of IFN-γ and IL-4 as well as for LAG-3 expression, as described in FIGS. 4a–4d. Columns represent the mean values (± SE) obtained in three separate experiments.
Figure 2B:
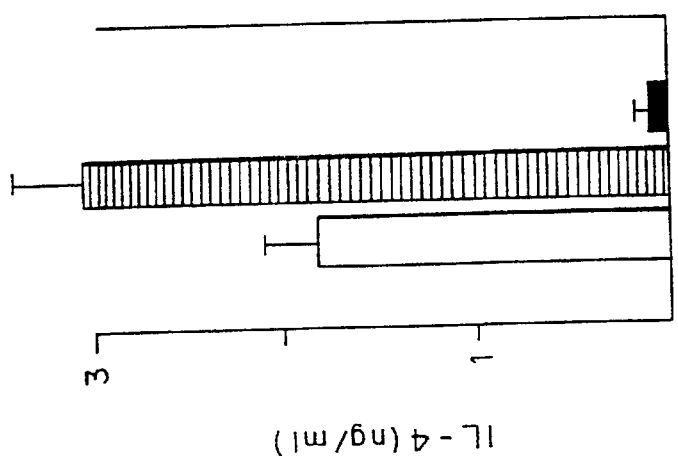
Figure 2A:
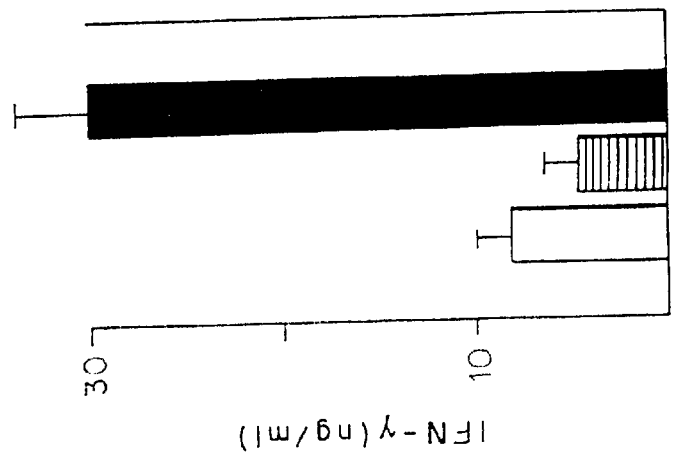

IL-12 is able to promote the development of Th1-type cells (Manetti, 1993). In contrast, IL-4 favors the preferential development of Th2-like cells (Maggi, 1992). Experiments were done to determine whether the addition of IL-12 or IL-4 in PBMC bulk culture could influence the expression of LAG-3 by antigen-activated T-cells. In these experiments, TT was used as antigen because of its ability to preferentially expand T-cells with mixed profile of cytokine production (Th0 cells) (Hsieh et al, 1993). As expected, IL-12 addition in PBMC culture favored the development of TT-specific T-cells able to produce higher amounts of IFN-$\gamma$ and lower amounts of IL-4 than the corresponding TT-specific T-cell lines generated in the absence of IL-12. Accordingly, the proportions of LAG-3$^+$ cells were significantly higher in IL-12-conditioned TT-specific T-cell lines than in parallel lines generated in the absence of IL-12 (FIGS. 2a–2c). On the other hand, the addition in PBMC bulk culture of IL-4 resulted in the development of TT-specific T-cell lines producing higher amounts of IL-4 and lower amounts of IFN-$\gamma$ than control TT-specific T-cell lines. However, the proportions of LAG-3$^+$ cells in TT-specific T-cell lines were not significantly affected by IL-4 conditioning (FIGS. 2a–2c).

Figure 3A:
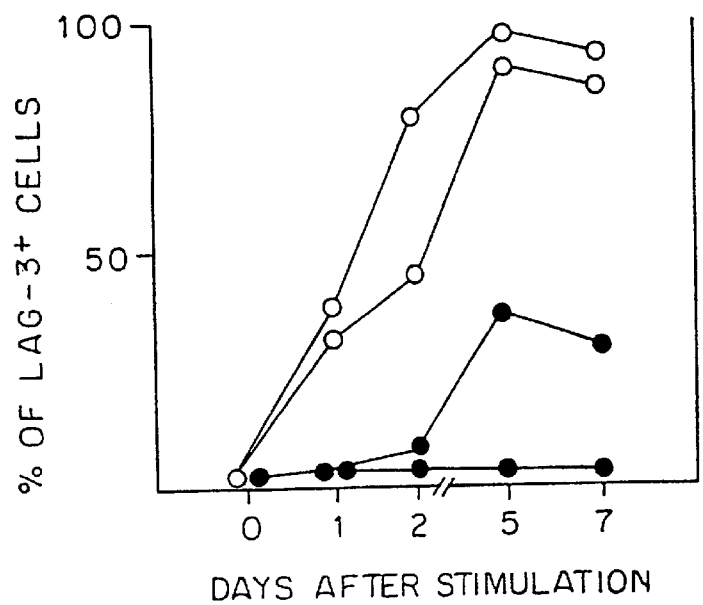
FIGS. 3a and 3b show the kinetics of membrane LAG-3 and CD30 expression by four $CD4^+$ T-cell clones. $CD4^+$ T-cell clones were generated from PBMC of normal donors, as described in Example 1. To assess the cytokine profile of each clone, T-cell blasts ($10^6$/ml) were stimulated for 36 hr with PMA (10 ng/ml) plus anti-CD3 antibody (100 ng/ml) and IFN-γ and IL-4 were quantitated in culture supernatants, as described in Example 1. T-cell clones able to produce IFN-γ but not IL-4, were classified as Th1-like; T-cell clones producing IL-4, but not IFN-γ, were classified as Th2-like; T-cell clones producing both IL-4 and IFN-γ were classified as Th0-like. Two Th1-like and two Th2-like $CD4^{30}$ T-cell clones were stimulated with PHA (1% v/v) plus IL-2 (20 U/ml) and assessed at 24 hr-intervals for both LAG-3 and CD30 expression by flow cytometry, as described in Example 1.
Figure 3B:
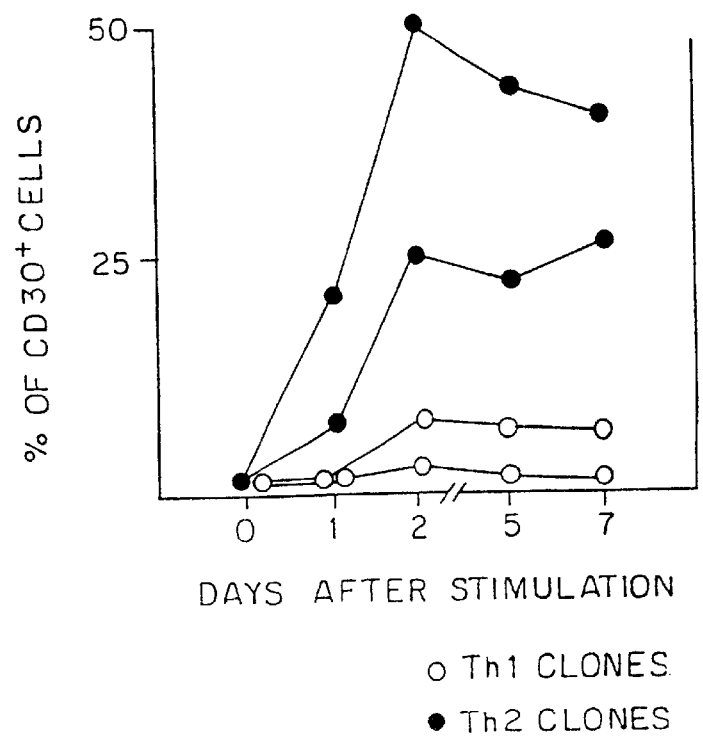
Figure 4:
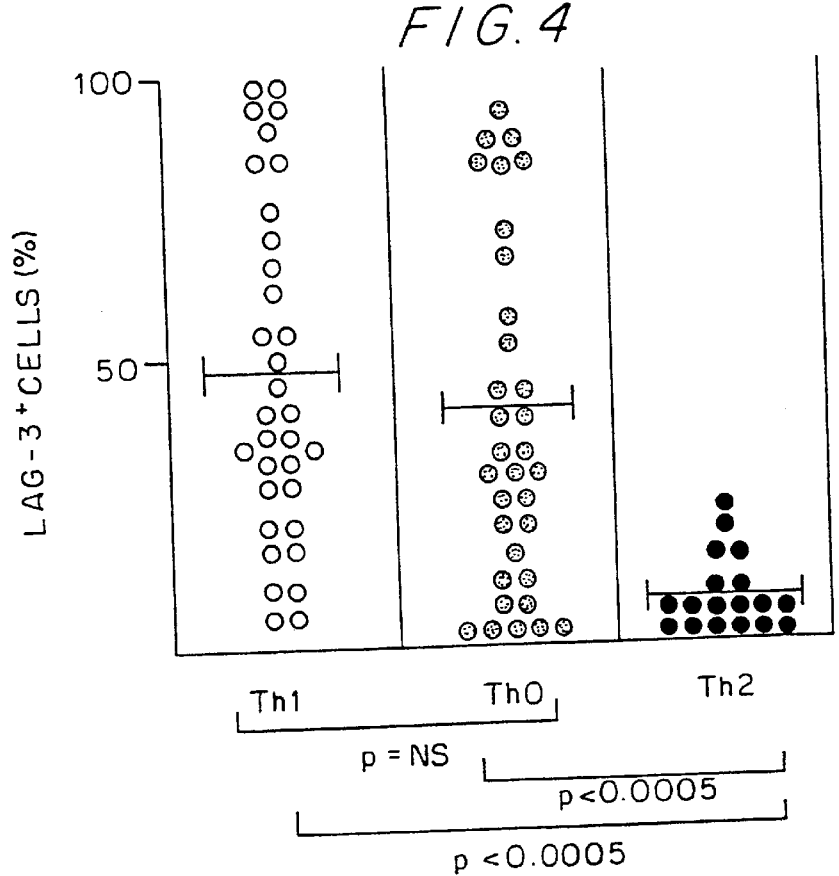
FIG. 4 shows the membrane LAG-3 expression by 84 $CD4^+$ T-cell clones (33 Th1-like, 33 Th0-like and 18 Th2-like) $CD4^+$ T-cell clones were generated, and categorized as Th1-like, Th0-like and Th2-like, as described in FIGS. 3a and 3b. Values represent proportions of T-cell blasts from each clone showing membrane LAG-3 expression on day 4 after activation with PHA plus IL-2.

Preferential LAG-3 Expression on the Membrane of T-Cell Clones Producing Th1-Type Cytokines The kinetics of surface LAG-3 and CD30 expression by four CD4$^{30}$ T-cell clones with already established profile of cytokine production (two Th1 and two Th2) was then investigated. The results of these experiments are presented in FIGS. 3a and 3b. When examined in the resting state (10 days after the last stimulation), all clones showed neither CD30 nor LAG-3 expression. Following stimulation with PHA plus IL-2, substantial proportions of T-cell blasts from the Th2 clones showed surface CD30 expression, whereas T-cell blasts from the Th1 clone did not. In contrast, under the same experimental conditions, LAG-3 expression was already detectable on a substantial proportion of Th1 cells on day 1 and it became maximal between day 2 and day 6 after activation. Similar results were obtained when T-cell clones were stimulated with insolubilized anti-CD3 antibody or PMA plus ionomycin. Based on these findings, a total number of 84 CD4$^+$ T-cell clones with established cytokine secretion profile (33 Th1, 33 Th0 , and 18 Th2), were stimulated with PHA plus IL-2 and assessed four days later for surface LAG- 3 expression. The results of these experiments are summarized in FIG. 4. Under these experimental conditions, LAG-3 was expressed by most Th1 and Th0 clones, whereas the great majority of Th2 clones showed no or poor LAG-3 expression. Th2 clones which did not express membrane LAG-3 under these experimental conditions also lacked LAG-3 mRNA expression when assessed by PCR after stimulation of cells with PHA (1% v/v) and IL-2 (20 U/ml) for 24 hrs. $CD4^+$ Th1-like and $CD8^+$ T-cell clones did show LAG-3 mRNA expression (570 bp band on agarose gel).

Figure 5:
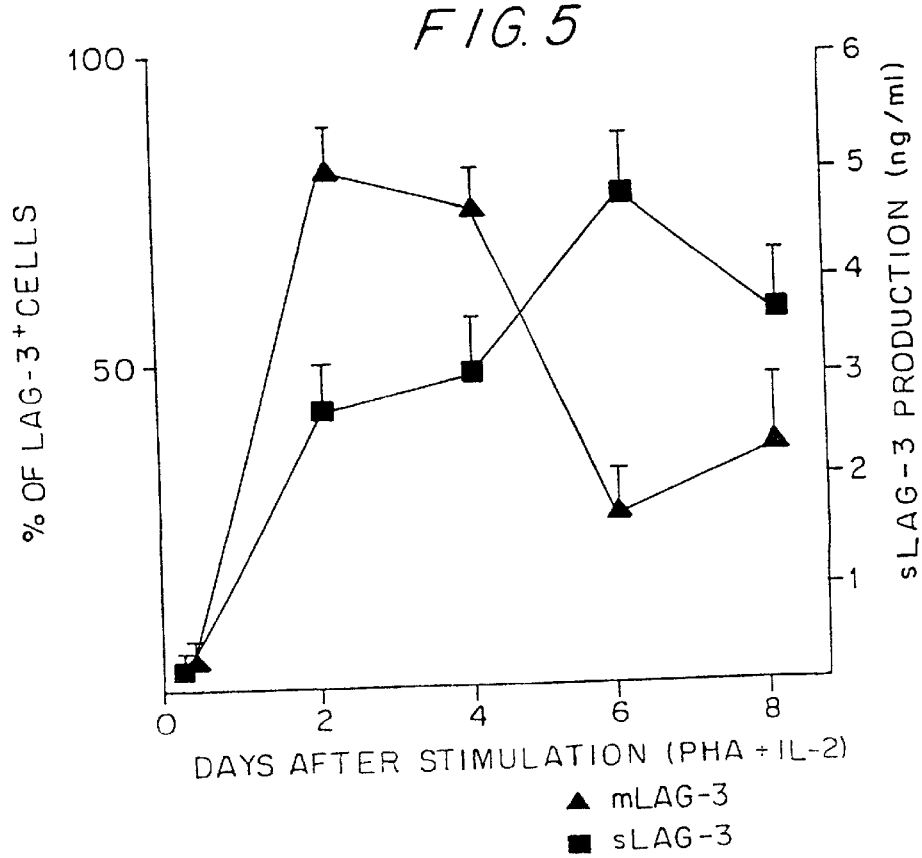
FIG. 5 shows the kinetics of soluble LAG-3 production by $CD4^{30}$ Th1-like clones stimulated with PHA plus IL-2. Membrane LAG-3 (mLAG-3) expression by T-cell blasts was assessed by flow cytometry (see also FIGS. 1a–1d). Soluble LAG-3 was measured into the cell-free supernatants by an appropriate ELISA, as described in Example 1. Results represent mean values ± SE from five different T-cell clones.
Figures 6A, 6B:
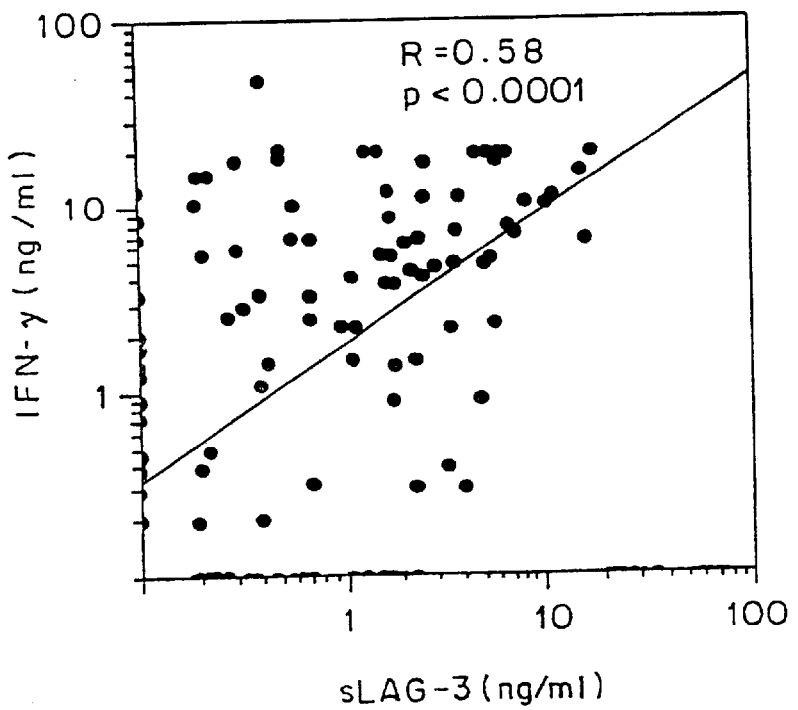
FIGS. 6a and 6b show the correlation between concentrations of soluble LAG-3, IFN-γ, and IL-4 produced by $CD4^{30}$ T-cell clones. A total number of 146 $CD4^{30}$ T-cell clones were stimulated for 4 days with PHA plus IL-2, and concentrations of soluble LAG-3, IFN-γ and IL-4 released into cell-free-supernatants were measured, as described in FIGS. 1a–1d and 4.

Release of a Soluble LAG-3 Molecule by T-Cell Clones Producing Th1-Type Cytokines The possibility that LAG-3 was released as soluble molecule in T-cell clone supernatants was also investigated. This was done by both an appropriate ELISA using a recombinant extracellular portion of LAG-3 molecule (D1–D2) FIG. 5 shows the kinetics of membrane LAG-3 expression and soluble LAG-3 production by five representative clones (3 Th1 and 2 Th0 ). Membrane LAG-3 was fully expressed on the cell membrane between day 2 and 4 following activation with PHA plus IL-2 and then declined, whereas soluble LAG-3 was already found into day 2 supernatant and its concentrations became still higher between day 4 and day 8. Concentrations of soluble LAG-3 were then measured in the supernatants of large panels of activated $CD4^+$ T-cell clones and compared with concentrations of IFN-$\gamma$ and IL-4 present in the same supernatants. There was a significant positive correlation between concentrations of soluble LAG-3 and IFN-$\gamma$, whereas an inverse correlation between production of soluble LAG-3 and IL-4 was observed (FIGS. 6a and 6b).

Delayed Type Hypersensitivity (DTH) Reaction

The delayed type hypersensitivity (DTH) reaction is a reliable method of evaluating the cell-mediate immune response. DTH is manifested in the skin by an erythematous indurated reaction maximal 24–48 hours after the intradermal injection of the antigen, e.g., tetanus toxoid. Both elimination of the infecting organism and the DTH reaction occurs as a result of interaction between the specifically sensitized lymphocytes (especially T cell presenting a Th1 profile) and specific antigen. This leads to the secretion of lymphokines that activate macrophages directly to eliminate intracellular organisms and cause the secretion of inflammatory mediators.

Six female Cynomolgus monkeys have been vaccinated with tetanus toxoid via intramuscular route. After 28 days, the efficacy of the vaccination was verified by inducing a DTH reaction using the Multitest CMI Merieux. In all animals, induration was measured at the site of injection of tetanus toxoid antigen and Tuberculin antigen at 1 to 7 days after antigen application. Twenty eight days after the first DTH, monkeys were injected i.v. with 10 mg/kg of either anti-LAG-3 mAb (11E3, Group I) or anti-FSH mAb (used as isotype negative control, Group 2). DTH reaction was induced 30 min after antibody injection using the Multitest CMI Merieux.

Figure 7A:
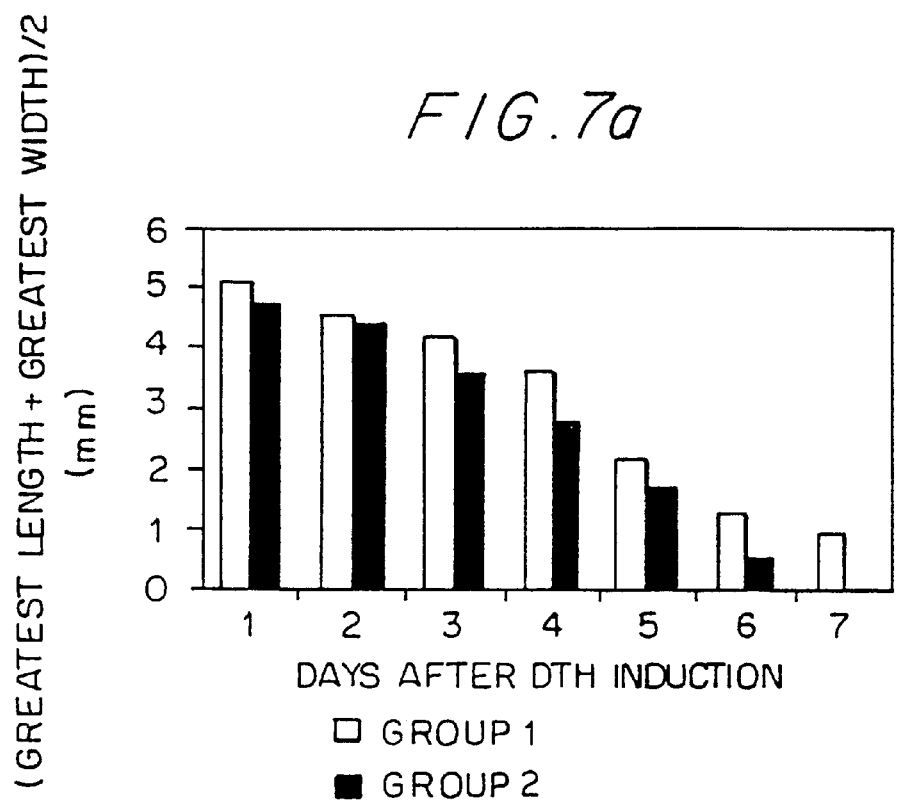
FIGS. 7A and 7B show the delayed-type hypersensitivity (DTH) score of monkeys intradermally receiving tetanus toxoid. The first DTH (FIG. 7A) was performed using two groups of 3 animals receiving only TT. The second DTH (FIG. 7B) was performed in animals in which anti-LAG-3 monoclonal antibodies or anti-FSH antibodies as isotype matched negative control were previously administered.

Animals reacted positively at the site of TT injection with little or no erythema (without appreciable induration) was observed at the site of injection of the negative control, i.e., the glycerin control present in the Multitest CMI Merieux (FIG. 7A). After the first DTH all animal reactions were strongest at 24 hours and then declined, and all were negative 7 days after induction.

Figure 7B:
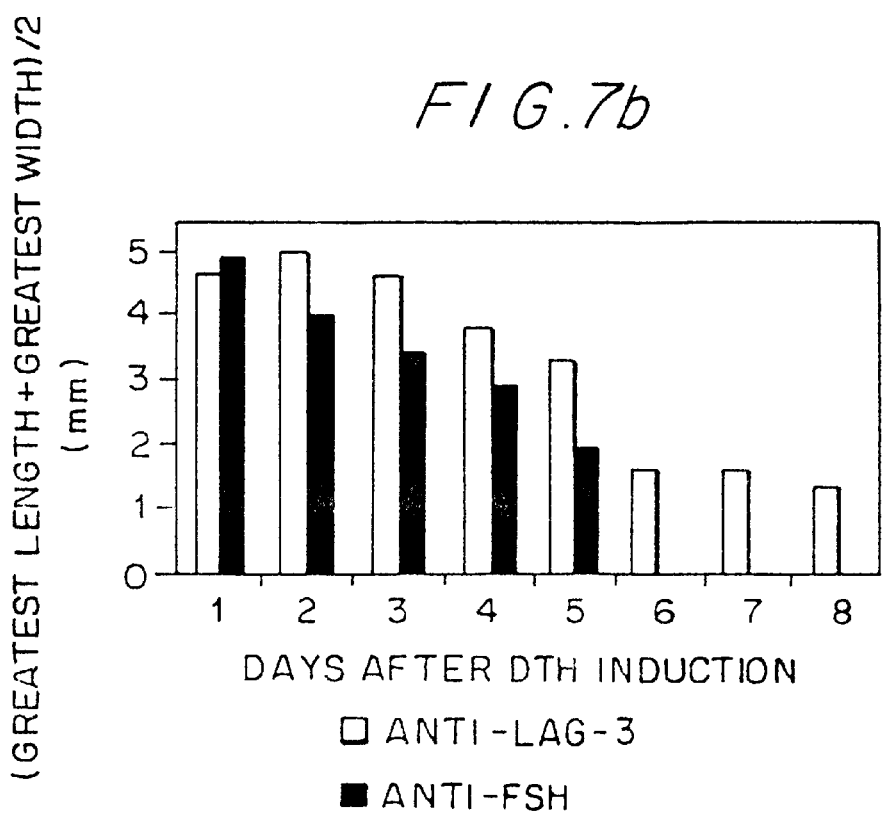

After the second DTH induction all animals responded positively at the site of injection of TT (FIG. 7B). In the control group receiving anti-FSH antibody the response was similar to that observed during the first DTH. In the group treated with anti-LAG-3 mAb (11E3), the DTH score from Day 2 to Day 5 was stronger that in the control group and was prolonged, i.e. was still detected when no reaction was visible in the control group (Day 6 to Day 8).

This data indicates that anti-LAG-3 antibodies can polarize the differentiation of naive Th cells towards Th1 in vivo and thus modulate an in vivo reaction which is commonly associated with Th1 cells. This observation is in agreement with the observation that anti-LAG-3 antibodies are able to prolong in vitro the proliferation of antigen specific T cell clones (Huard et al., 1996).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Triebel, F., S. Jitsukawa, E. Baixeras, S. Roman-Roman, C. Genevee, E. Viegas-Pequignot, and T. Hercend. 1990. LAG-3, a novel lymphocyte activation gene closely related to CD4. *J. Exp. Med.,* 171:1393.

2. Baixeras, E., B. Huard, C. Miossec, S. Jitsukawa, M. Martin, T. Hercend, C. Hauffray, F. Triebel, and D. Piatier-Tonneau. 1992. Characterization of the lymphocyte activation gene 3- encoded protein. A new ligand for human leukocyte antigen class II antigen. *J. Exp. Med.,* 176:327.

3. Huard, B., P. Gaulard, F. Faure, and F. Triebel. 1994A. Cellular expression and tissue distribution of the human LAG-3 encoded protein, an MHC class II ligand. *Immunogenetics,* 39:213.

4. Huard, B., M. Tournier, T. Hercend, F. Triebel, and F. Faure. 1994B. Lymphocyte-activation gene 3/major histocompatibility complex class II interaction modulates the antigenic response of $CD4^+$ T lymphocytes. *Eur. J. Immunol.,* 24:3216.

5. Huard, B., P. Prigent, F. Pages, D. Bruniquel, and F. Triebel. 1996. T-cell MHC class II molecules downregulate T-cell proliferation following LAG-3 binding. *Eur. J. Immunol.*, 26:1180–1186.

6. Mosmann, T. R., H. Cherwinski, M. Bond, W. Giedlin, and R. Coffman 1986. Two types of murine T-cell clone. I. Definition according to profiles of lymphokine activities and secreted proteins. *J. Immunol.*, 136:2348

7. Del Prete, G. F., M. De Carli, C. Mastromauro, R. Biagiotti, D. Macchi, P. Falagiani, M. Ricci, and S. Romagnani. 1991. Purified protein derivative of Myobacterium tuberculosis and excretory/secretory antigen(s) of Toxocara canis expand in vitro human T-cells with opposite (type 1 T helper or type 2 T helper) profile of cytokine production. *J. Clin. Invest.*, 88:346.

8. Sher A., and R. Coffman. 1992. Regulation of immunity to parasites by T-cells and T-cell-derived cytokines. *Annu. Rev. Immunol.*, 10:385.

9. Romagnani, S. 1994. Lymphokine production by human T-cells in disease states. *Annu. Rev. Immunol.*, 12:227.

10. Del Prete, G. F., M. De Carli, F. Almerigogna, C. K. Daniel, M. M. D'Elios, G. Zancuoghi, F. Vinante, G. Pizzolo, and S. Romagnani. 1995A. Preferential expression of CD30 by human CD4+ T-cells producing Th2-type cytokines. *FASEB J.*, 9:81.

11. Smith, C., T. Davis, D. Anderson, L. Solam, M. P. Beckmann, R. Jerzy, S. K. Dower, D. Cosman, and R. G. Goodwin. 1990. A receptor for tumor necrosis factor defines an unusual family of cellular and viral proteins. *Science*, 248:1019.

12. Manetti, R., P. Parronchi, M. -G. Guidizi, M. -P. Piccinni, E. Maggi, G. Trinchieri, and S. Romangani. 1993. Natural killer cell stimulatory factor (interleukin 12) induces T helper type 1 (Th1 )-specific immune responses and inhibits the development of IL-4 producing the cells. *J. Exp. Med.*, 177:1199.

13. Manetti, R., F. Gerosa, M. -G. Giudizi, R. Biagiotti, P. Parronchi, M. -P. Piccinni, S. Sampognaro, E. Maggi, S. Romagnani, and G. Trinchieri. 1994. Interleukin 12 induces stable priming for interferon-γ (IFN-γ) production during differentiation of human T helper (Th) cells and transient IFN-γ production in established Th2 cell clones. *J. Exp. Med.*, 179:1273.

14. Maggi, E., Parronchi, P., Manetti, R., Simonelli, C., Piccinni, M. -P., Santoni-Rugiu, F., De Carli, M., Ricci, M., Romagnani, S. 1992. Reciprocal regulatory role of IFN-γ and IL-4 on the in vitro development of human Th1 and Th2 clones. *J. Immunol.*, 148:2142.

15. Hsieh, C. -S., Macatonia, S. E., Tripp, C. S., Wolf, S. F., O'Garra, A., Murphy, K. M. 1993. Development of Th1 CD4+ T-cells through IL-12 produced by Leisteria-induced macrophages. *Science*, 260:547.

16. Swain, S. L. 1993. IL-4 dictates T-cell differentiation. *Res. Immunol.*, 144:619.

17. Seder, R. A., Paul, E. W., Davis, M. M., Fazekas de St Groth, B. 1992. The presence of interleukin-4 during in vitro priming determines the lymphocyte-producing potential of CD4+ T-cells from T-cell receptor transgenic mice. *J. Exp. Med.*, 176:1091.

18. Reiner, S. L., Locksley, R. M. 1993. The worm and the protozoa: stereotyped responses or distinct antigens? *Parasitol. Today*, 9:268.

19. Maggi, E., Annunziato, F., Manetti, R., Biagiotti, R., Giudizi, M. -G., Ravina, A., Almerigogna, F., Boiani, N., Alderson, M., Romagnani, S. 1995. Activation of HIV expression by CD30 triggering in CD4+ T cells from HIV-infected individuals. *Immunity* 3:251–5.

20. Del Prete, G. -F., De Carli, M., D'Elios, M. M., Daniel, K. C., Alderson, M., Smith, C. A., Thomas, E., Romagnani, S. 1995B. CD30-mediated signalling promotes the development of human T helper type 2-like T cells. *J. Exp. Med.* 182:1655–1651.

21. Romagnani, S., Del Prete, G. -F., Maggi, E., Caligaris Cappio, F., Pizzolo, G. 1995. CD30 and type 2 T helper (Th2) responses. *J. Leukocyte Biol.*, 57:726.

22. Pizzolo, G., Vinante, F., Morosato, L., Naali, G., Chilosi, M., Gandini, G., Sinicco, A., Raiteri, S., Semenzato, G., Stein, H., Perona, G. 1994. High serum level of soluble form of CD30 molecule in the early phase of HIV-1 infection as an independent predictor of progression to AIDS. *AIDS*, 8:741.

23. Caligaris Cappio, F., Bertero, T., Converso, M., Stacchini, A., Vinante, F., Romagnani, S., Pizzolo, G. 1995. Circulating levels of soluble CD30, a marker of cells producing Th2 type cytokines, are increased in patients with Systemic Lupus Erythematosus and correlate with disease activity. *Clin. Exp. Rheumatol.* 13:339–43.

24. Clerici, M., Shearer, G. 1993. A Th1/Th2 switch is a critical step in the etiology of HIV infection. *Immunol. Today*, 14:107.

25. Mills, J. A. 1994. Systemic Lupus Erythematosus. *N. Engl. J. Med.*, 330:1871.

26. Griffin, D., Ward, B. J. 1993. Differential CD4 T-cell activation in measles. *J. Infect. Dis.*, 168:275.

27. Selmaj, K., Raine, C. S., Cannella, B., Brosnan, C. F. 1991. Identification of lymphotoxin and tumor necrosis factor in multiple sclerosis lesions. *J. Clin. Invest.*, 87:949.

28. Liblau, R. S., Singer, S. M., McDevitt, H. O. 1995. Th1 and Th2 CD4+ T cells in the pathogenesis of organ-specific autoimmune diseases. *Immunology Today*, 16:34–38.

29. Cole, E. S., Lee, K., Lauziere, K., Kelton, C., Chappel, S., Weintrau, B., Ferrara, D., Peterson, P., Bernasconi, R., Edmunds, T., Richards, S., Dickrell, L., Kleeman, J. M., McPherson, J. M., Pratt, B. M. 1993. Recombinant human thyroid stimulating hormone: Development of a biotechnology product for detection of metastatic lesions of thryoid carcinoma. *Biotechnology*, 11:1014–1023.

30. Urlaub, G., and Chasin, L. A. 1980. Isolation of Chinese hamster cell mutants deficient in dehydrofolate reductase activity. *Proc. Natl. Acad. Sci. (USA)*, 77:4216–4220.

31. Kuchroo, V. R. et al., 1995. *Cell*, 80:707–718.

32. Annunziato, F. et al., 1996. *FASEB J.*, 10:769–775.

33. Mosmann, T. R. and Sad, S., 1996. *Immunol. Today*, 17:138–146.

34. De Bruijn, M. L. H. et al., 1991. *Eur. J. Immunol.*, 21:2963–2970.

35. Macatonia, S. E. et al., 1989. *J. Exp. Med.*, 169:1255–1264.

36. Oldstone, M. B. A. et al., 1986. *Nature*, 321:2329–243.

37. Kast, W. M. et al., 1989. *Cell*, 59:603–614.

38. Riddell, S. R. et al., 1992. *Science*, 257:238–241.

What is claimed is:

1. A method for diagnosing a Th1-mediated disease or disorder, comprising the steps of:

reacting a sample of human fluid, derived from an individual suspected to suffer from a Th1-mediated disease, with an antibody, or fragment thereof, specific for soluble LAG-3; and measuring the amount of soluble LAG-3 that is bound to the soluble LAG-3 specific antibody, or a fragment thereof, wherein an elevated amount of soluble LAG-3 relative to the amount of soluble LAG-3 in a sample of human fluid derived from an individual not suffering from a Th1-mediated disease or disorder is diagnostic for the presence of a Th1-mediated disease or disorder.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

TCTCTCAGAG CCTCCGACTG GGTCATTTTG                              30

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

CTGGATGTGG ACGGTATAGG TAGACGTCCT                              30